United States Patent
Ghiassi et al.

(10) Patent No.: US 6,336,044 B1
(45) Date of Patent: Jan. 1, 2002

(54) RELIABLE BODY FAT MEASUREMENT IN SELF-SERVICE HEALTH PARAMETER MEASURING SYSTEM

(75) Inventors: Hessam Ghiassi, Rockville; Robert D. Rosenthal, Gaithersburg, both of MD (US)

(73) Assignee: Futrex Inc., Gaithersburg, MD (US)

( * ) Notice: Subject to any disclaimer, the term of this patent is extended or adjusted under 35 U.S.C. 154(b) by 0 days.

(21) Appl. No.: 09/393,817

(22) Filed: Sep. 10, 1999

Related U.S. Application Data

(60) Provisional application No. 60/099,975, filed on Sep. 11, 1998.

(51) Int. Cl.$^7$ ................................................. A61B 6/00
(52) U.S. Cl. .................... 600/473; 600/476; 600/479; 600/480; 600/481; 600/440; 600/492; 600/495; 606/12; 606/13; 359/503; 359/515; 359/516; 359/517; 250/316.1
(58) Field of Search ................................. 600/300, 310, 600/311, 317, 326, 473, 407, 344, 476, 479, 480, 481, 490, 492, 495, 500, 335, 502–505; 606/12, 13, 1, 9, 10, 11; 607/1; 128/99.1, 869, 878, 879, 881; 554/503, 515, 510, 517; 250/316.1; 5/601, 617, 621, 623, 646, 613

(56) References Cited

U.S. PATENT DOCUMENTS

| | | | | |
|---|---|---|---|---|
| 4,928,014 A | * | 5/1990 | Rosenthal | 250/341.5 |
| 5,014,713 A | * | 5/1991 | Roper et al. | 128/664 |
| 5,410,471 A | * | 4/1995 | Alyfuku et al. | 128/708 |
| 6,134,458 A | * | 10/2000 | Rosenthal | 600/310 |
| 6,151,516 A | * | 11/2000 | Kiani-Azarbayjany et al. | 600/322 |

* cited by examiner

Primary Examiner—Marvin M. Lateef
Assistant Examiner—Jeoyuh Lin
(74) Attorney, Agent, or Firm—Rothwell, Figg, Ernst & Manbeck

(57) ABSTRACT

In a self-service health parameter measuring apparatus and method, a person's elbow is placed at a spatial reference point, and means surrounding a user's forearm locate an infrared body fat apparatus measurement point at a substantially fixed distance from the spatial reference point. Motor drive means adjustably tighten or loosen a cuff around an upper arm so that measurements on each user are made at substantially the same pressure of the measuring apparatus against a forearm irrespective of the size of the arm. In a preferred form, the preselected measurement pressure is achieved by inflating the cuff to a maximum level, and allowing deflation. Measurement is made when a lower, second preselected level is reached. Blood pressure is also measured in connection with the inflation and deflation operation. Further health parameters may be measured.

18 Claims, 5 Drawing Sheets

RELIABLE BODY FAT MEASUREMENT IN SELF-SERVICE HEALTH PARAMETER MEASURING SYSTEM

CROSS-REFERENCE TO RELATED APPLICATION

Applicants claim the benefit of U.S. Provisional application Ser. No. 60/099,975, filed Sep. 11, 1998.

BACKGROUND OF THE INVENTION

1. Field of the Invention

The present invention relates to an apparatus for self-service measuring of health parameters, e.g. body fat, using near infrared measurement preferably included in an apparatus for measuring other health parameters also, such as blood pressure and heart rate.

2. Description of Related Art

"Health parameters" herein refers to such values as blood pressure and pulse rate. These are items which can be measured in a self-service apparatus in such places as a pharmacy. Such apparatus can be operated by lay people such as retail customers simply by following the instructions printed on a unit. The customer places an arm in a blood pressure measuring unit and pushes a start button. After a fraction of a minute, blood pressure and heart rate values appear on a display. The public acceptance of such self-test instrumentation is a direct result of the public's interest in fitness. There is great demand for self-testing of blood pressure and pulse rate. Demand for self-testing of other parameters is growing. Body fat testing in now an important measurement. Body fat testing is often performed in routine health screening. Additional parameters may also be measured in accordance with the present invention. Those parameters may not yet be reported outside of a research context due to regulatory constraints. One example is body water.

Commonly available apparatus for body fat testing, for example the FUTREX-5000 series of instruments is widely used to perform near-infrared body fat measurement. This apparatus requires a trained operator to perform the measurements. The body fat testing is performed at the midpoint of the biceps, as further explained in commonly assigned U.S. Pat. No. 4,850,365, the disclosure of which is incorporated herein by reference. A trained operator is needed since the proper site at the biceps for measurement must be located and a "light wand" must be placed at that site. The light wand utilizes at least two wavelengths of light, and an infrared interactance technique is use to translate the measurements of infrared light into body fat measurements.

Technical literature also shows that accurate measurement of percent of body fat can also be performed at other body sites. Measuring at the midpoint of the triceps is disclosed in N. Conway, *A New Approach for the Estimation of Body Fat Composition: Infrared Interactants,* and *American Journal of Chemical Nutrition* 40: December 1984, pp. 1123–110. To provide an apparatus capable of determining this location automatically would be both difficult and expensive. It would be most advantageous if an easily defined site could be found that at which body fat could be measured. A distinct location clearly defined in relation to well-defined locations in the human body would permit design of an automated apparatus.

SUMMARY OF THE INVENTION

It is therefore a particular advantage of the present invention to provide an apparatus for self-service measuring of percentage body fat by an untrained person.

It is a further particular advantage of the present invention to provide an apparatus including means for applying infrared radiation to a person's arm for self-service measuring of body fat.

It is also a particular advantage of the present invention that self-test of body fat measurement may be combined with automated blood pressure and pulse measurement.

In accordance with the present invention, it has been discovered that there is a site which can be automatically determined by a health parameter measurement apparatus so that performance of body fat measurement could be made by a consumer at a self-service apparatus. The site is a fixed distance from the elbow on a person's triceps.

Briefly stated, in accordance with the present invention, there is provided an apparatus in which a person may insert an arm into a fixture, the fixture providing a reference location for the elbow, and in which a infrared measurement means is placed at the fixed distance from the elbow. In a preferred form, an arm tube is provided which is capable of accommodating a large range of arm sizes. This range could, for example, be the three standard deviation range for a population of arms. Mechanical means, such as a motor pulley arrangement wrap the mechanism around the arm of a person. This wrapping is similar to placing sphygmomanometer cuff around the patient's arm for blood pressure measurement. Indeed, the wrapping apparatus might comprise a blood pressure cuff modified to permit body fat measurement. A light wand is contained against the arm in a proper measurement position. The measurement may be made during a blood pressure measurement. The same apparatus may measure heart rate in a conventional manner. The apparatus could also contain means for doing known radiometric measurement through a finger for analytes of interest. Automatic weight measurement may also be provided.

BRIEF DESCRIPTION OF THE DRAWINGS

The means through which the foregoing advantages and feature of invention are achieved are pointed out with particularity in the claims forming the concluding portion of the specification. The invention, both as to its organization and manner of operation may be understood by reference to which the following description taken in connection with the following drawings.

Of the drawings.

DETAILED DESCRIPTION OF THE PREFERRED EMBODIMENTS

Figure 1:
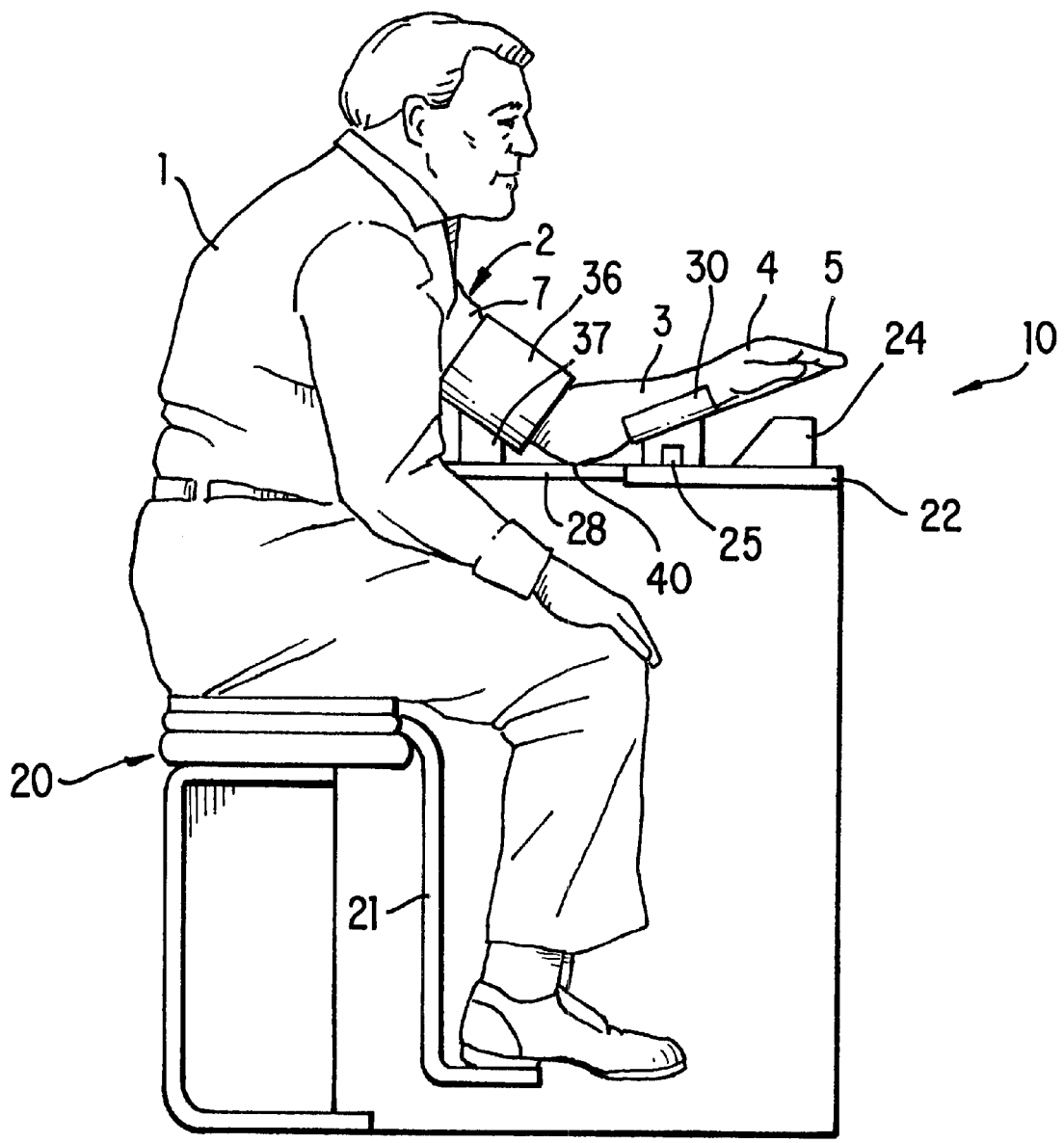
FIG. 1 is a perspective illustration of a user employing apparatus constructed in accordance with the present invention.
Figure 2:
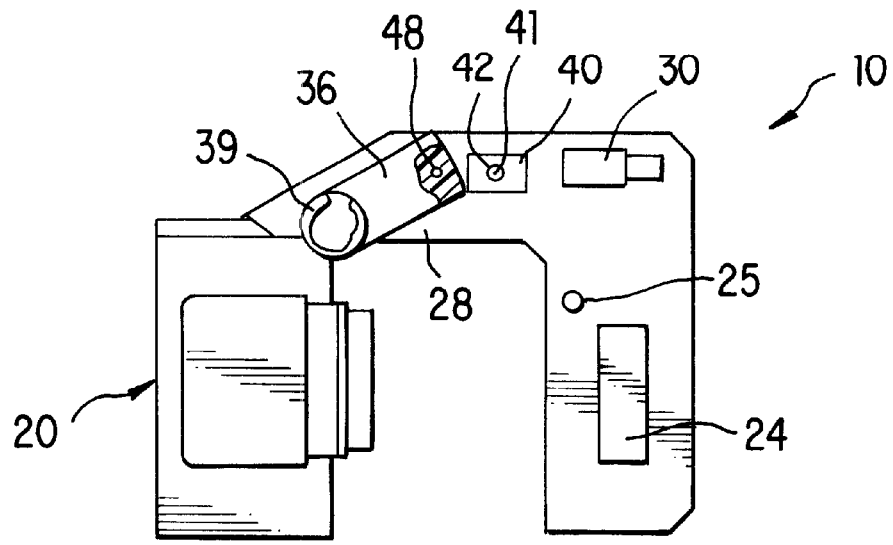
FIG. 2 is a plan view of the apparatus without a user present.

FIG. 1 is a perspective view of a user 1 employing an apparatus 10 constructed in accordance with the present invention. FIG. 2 is a plan view of the apparatus illustrated in FIG. 1. In the figures, the same reference numerals are used to denote the same elements.

In order to provide for a measurement to be made at a fixed point from an elbow, the apparatus 10 provides for a user 1 to place an arm 2 in a position such that a forearm 3 and hand 4, including fingers 5, are rested, an elbow 6 is maintained at a reference location, and an upper arm 7 is positioned for measurements to be made thereon. In the present description, "elbow 6" means an end of a bone that depresses switch 42 (described below).

The apparatus 10 comprises a seat 20 for receiving the user 1. A display counter 22 supports a display 24. Display 24 may include conventional light emitting diodes to display numbers to the user and may also include conventional warning, instruction and informational displays. An arm support panel 28 is located to a side of the seat 20. The display 24 is placed with respect to the seat 20 to allow ingress and egress from the apparatus 10 by the user. The display lettering on display 24 is made large enough for viewing. A nominal distance between the display 24 to the front of the seat 20 is 16 inches. The angle of display 24 is approximately 10°–30° from horizontal. A "start" button 25 is located within arm's reach of a user 1.

A seat extension 21 is incorporated in the seat 20. A user 1 rests his or her heels on the extension 21 to apply full body weight to the seat 20. In the preferred embodiment, the seat 20 comprises a scale providing electrical outputs so that weight may be shown on the display 24.

The arm support panel 28 includes a forearm support 30 having a forearm rest 32. A hand support 33 is included in embodiments in which a measurement is made by placing a user 1's fingers 5 in a finger chemistry tester 34. The forearm rest 32 is angled with respect to the arm support panel 28. The upper arm 7 is received in an arm tube 36 supported to the arm support panel 28 by an arm tube support 37. The arm tube 36 and the forearm support 30 are angled to support the upper arm 7 and the forearm 3 respectively so that the elbow 6 will be placed in an elbow support 40. The elbow support 40 need not be a discrete element from the arm support panel 28. The elbow support 40, as seen in FIG. 2, includes a spatial reference point 41, a fixed distance from which the infrared measurement will be made. A limit switch 42 is located at the spatial reference point 41. By maintaining the forearm 2 at a low angle, a bone at the elbow 6 will protrude for hitting the limit switch 42.

Again, the arm tube 36 is designed to fit a wide range of people. On smaller people, the arm tube 36 will cover most of the upper arm 7. On larger people, the upper arm 7 will be covered nearer the elbow. In each case, the arm tube 36 provides for covering the area of the upper arm above described fixed distance from the elbow 6. A cuff 39 inside the arm tube 36 surrounds the upper arm 7. It is necessary to stop cuff inflation automatically for each user 1 irrespective of the user 1's arm size. To this end, as seen in FIG. 2, an arm sensor 48 is mounted to the cuff 39 adjacent the elbow 6. The sensor 48 senses the cuff 39 being fully open with respect to a particular user 1. The sensor 48 may comprise, for example, a strain gauge coupled to a well-known sensor circuit.

Figure 3:
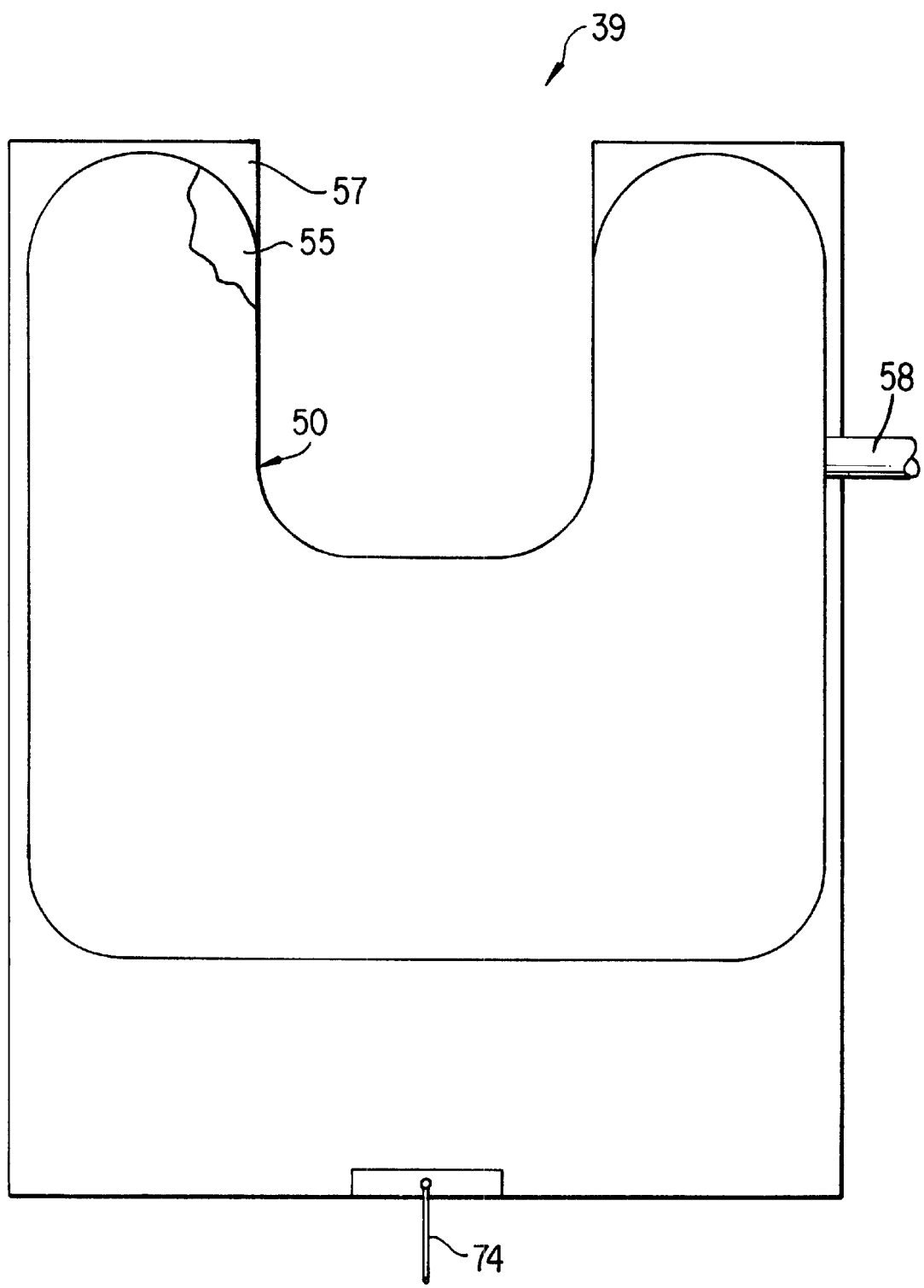
FIG. 3 is a plan view of an air bladder assembly to be formed into an inflatable cuff.

FIG. 3 is a plan view of an air bladder assembly 50 suitable for use as the cuff 39 in the arm tube 36. Air bladder assembly 50 consists of an air bladder 55 having a thin plastic sheet 57 formed thereon. The thin plastic memory sheet 57 has a "memory". The air bladder 55 is pneumatically connected to an air tube 58. The air tube 58 is connected to a source of air pressure and exhaust for inflating and deflating the air bladder 55 in a conventional manner. When the cuff 39 is rolled to fit in the arm tube 36, and the memory sheet 57 is consequently rolled upon itself, the inherent mechanical characteristic of the memory sheet 57 is to try to return to its initial configuration as a flat shape. The wrapping mechanism, including a cable 74, is described below with respect to FIGS. 6 and 7.

Figure 4:
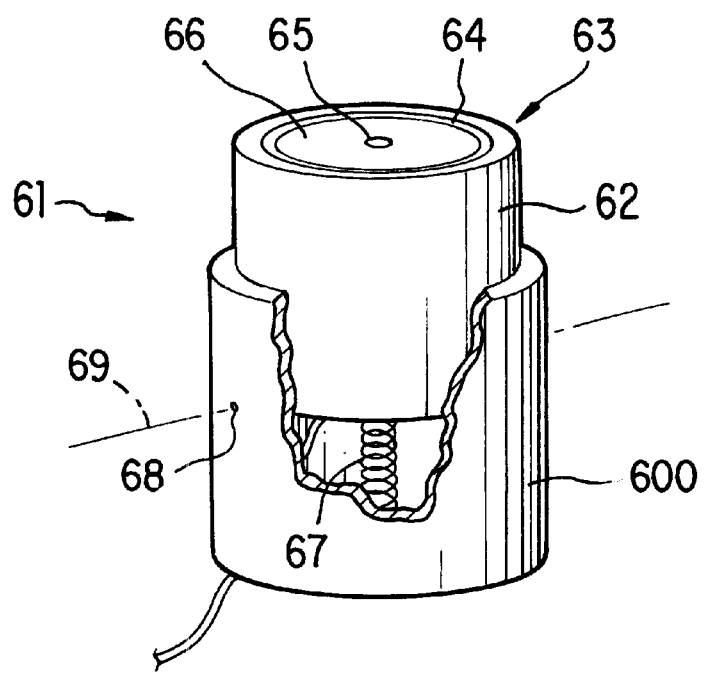
FIG. 4 is an illustration of an infrared measurement wand included in the present apparatus.
Figure 5:
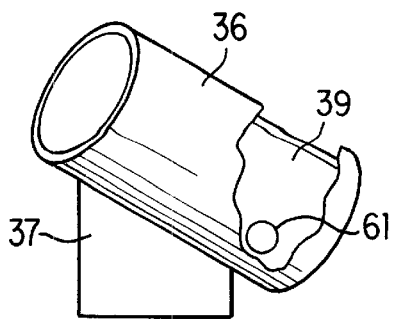
FIG. 5 is a detail of FIG. 1, partially broken away, illustrating positioning of the light wand assembly of FIG. 4 in the cuff.

FIG. 4 illustrates a light wand assembly 61 applying infrared radiation at a designated position 60 (FIG. 5). The designated position is on the triceps in the upper arm 7. The above-described fixed distance from the elbow 6 to the center of a light emitting head 63 (below) is 4.5 inches ±0.3 inches. A light wand 62 in the light wand assembly 61 includes an emitter-receiver of unit 63 used in prior art body fat measurement systems, for example, the Futrex-6100/XL. This is a model requiring operation by a trained individual for proper placement of a light wand for measurement of body fat. In the present invention, the emitter-receiver unit 63 is received in a surrounding holder 62. The emitter-receiver unit 63 includes an infrared emitter 64 emitting a plurality of infrared frequencies. The emitter 64 is annular and surrounds a circular detector 65.

The emitter 64 and detector 65 are separated by opaque material in a transverse face 66 of the emitter-detector unit 63. As seen with respect to FIG. 5 below, the light wand assembly 62 is mounted to the cuff 39 so that the transverse face 66 will face the designated point 60 on the upper arm 7 of a user 1. A spring 67 in the holder 62 biases the emitter-detector unit 63 in a direction that will be toward an upper arm 7 of a user 1. Pivot means 68 having a pivot axis 69 couple the emitter-detector unit 63 to the holder 62 so the face 66 may be flush with an upper arm 7. The pivot means 68 may include a pin-in-slot arrangement on diametrically opposed sides of the holder 62.

The well-known infrared interactance technique uses a plurality of wavelengths. The emitter 64 may provide a number of wavelengths matched to the processing to be used. In the present embodiment, the emitter 64 provides six different infrared wavelengths. The emitter 64 is gimbaled in a collar 600 by resilient means such as springs 66. Since the collar 600 is resiliently mounted with respect to the cuff 39, a constant pressure is exerted against the upper arm 7 for further reliability in operation.

FIG. 5 is a partial detailed illustration of FIG. 1, partially broken away, illustrating the mounting of the light wand assembly 61 in the cuff 39. The transverse face 66 is provided for contacting the upper arm 7 to provide infrared radiation at the above-described fixed distance from the elbow 6.

Figure 6:
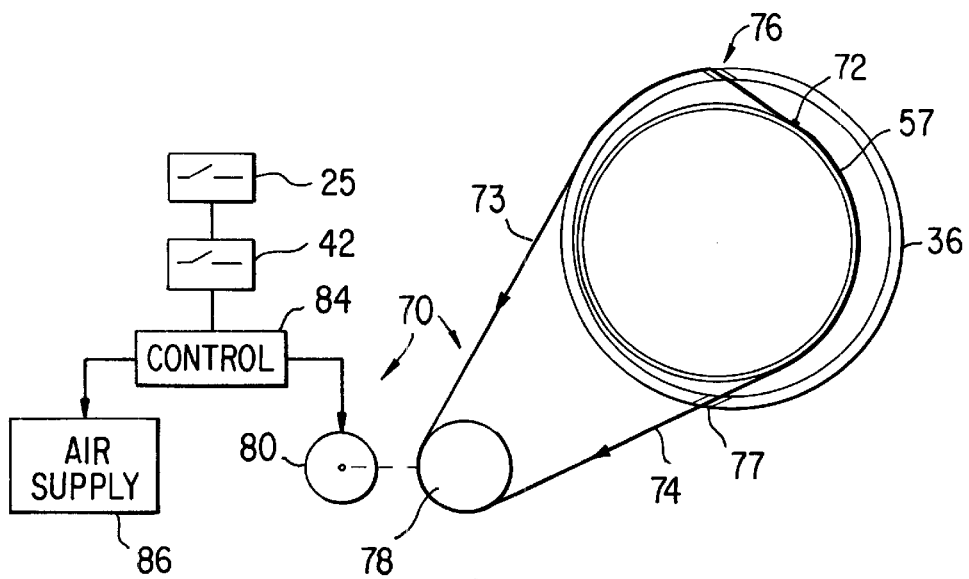
FIGS. 6 and 7 are each a cross-sectional view normal to an axis of an arm tube of the cuff in the open position.
Figure 7:
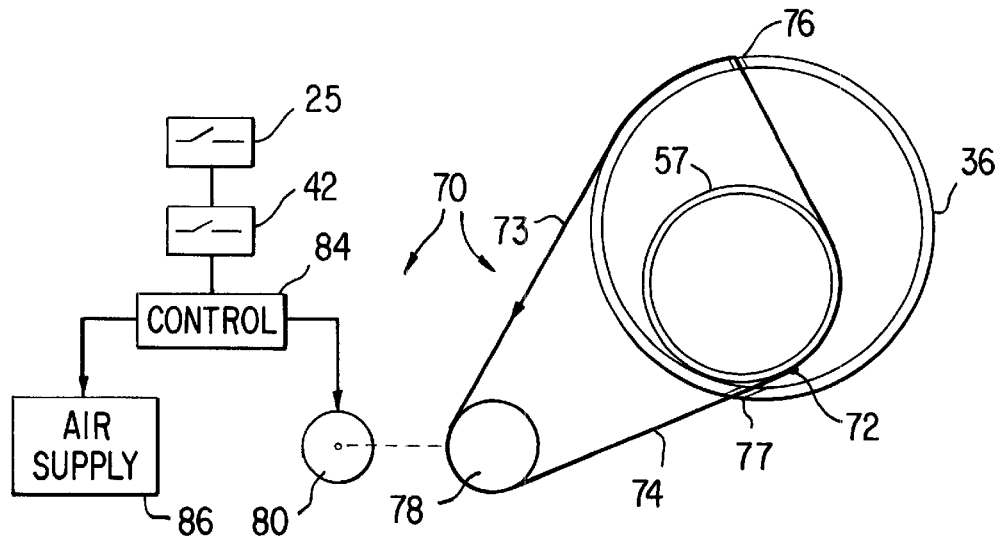

FIGS. 6 and 7 are each cross-sectional views in a plane normal to an axis of the arm tube 36. Within the arm tube 36 is a winding mechanism 70. The winding mechanism 70 causes the thin plastic memory sheet 57 to roll into itself, consequently, the winding mechanism 70 automatically closes the cuff 39 around an arm 2.

In FIG. 6, for clarity, only the memory layer 57 of the cuff 39 is illustrated. The memory layer 57 preferably has a circumference greater than that of the inner circumference of the tube 36. Preferably, one end in the circumferential direction of the memory layer 57 extends over another. The resulting outer end has a cable attachment point 72 to which first and second cables 73 and 74 are attached. The cable 73 extends from the cable attachment point 72 through a first aperture 76 in the tube 36 and extends over the outside of the tube 36 and is fixed to a motor pulley 78 driven by a motor 80. The cable 74 is also fixed to the cable attachment point 72 and runs through an aperture 77 in the tube 36 to the pulley 78.

In it ambient state, the memory sheet 57 is fully open. More specifically, the memory sheet 57 is open to the full extent allowed by the cable 74. The length of the cable 74 between the pulley 78 and the cable attachment point may be adjusted to determine the maximum opening. After the switch 42 indicates the arm 2 is in place, in order to tighten the memory sheet 57 around the arm, a switch, for example the start switch 25 (FIGS. 1 and 2) is closed and the motor 80 is activated, and the pulley 78 is rotated clockwise as seen in FIG. 6 to draw the cable 74 around the pulley 78. This action pulls upon the cable connection point 72 and pulls the memory layer 57 further over upon itself. To loosen the cuff 39, the motor 80 is actuated so that the pulley 78 is rotated in a counter clockwise direction to pull the memory layer 57 back to its open position.

The sensor 48 is coupled to a microprocessor 82 in a control unit 84. The sensor senses openness of the cuff 39 which correlates to pressure on the upper arm 7. The control unit stops the motor 80 when a correct degree of tightness at the cuff 39 is achieved. A microprocessor 82 may be included in the control unit 84. Alternative means, e.g. monitoring current drawn by the motor 80, could be used as an indication of appropriate tightness of the cuff 39 on the upper arm 7.

OPERATION

In operation, the user 1 sits on the seat 20 and inserts an arm 2 through the arm tube 36. The elbow 6 comes to rest on the elbow support 40. The forearm 3 and hand 4 rest on the forearm rest 32 and hand support 33. When the arm is properly inserted, the limit switch 42 is depressed by the bone in the elbow 6. When the unit senses an initial starting position by closure of the switch 42, the unit may instruct the user to actuate start button 25 [may be closed by depressing it] or an automatic start might be provided.

The motor 80 (FIG. 6) is energized, and the arm wrapping operation is performed. The blood pressure cuff 39 is inflated and a preselected pressure is reached. In a preferred form of the invention, torque value of the motor 80 is selected so that the motor 80 will stall when it drives the cuff 39 to a full wrap position around any size arm. The control unit 84 allows a time-out period so that the cuff 39 reaches a full wrap position, and then supplies a voltage to make the motor 80 act as a brake.

Pressure in the cuff 39 is gradually released in accordance with well-known blood pressure measurement techniques. The body fat measurement is made, i.e. the emitter 64 is energized, as the pressure decreases to a preselected level. It has been found that in this manner, a consistent pressure for each individual being measured is maintained. Many other forms of control could be used. For example, the control unit 84, after sensing proper closure of the memory sheet 57 via the sensor 48 may send a signal to an air supply 86 providing an output to the tube 58 (FIG. 3) in order to inflate the cuff 39. In this manner, the emitter 64 (FIGS. 4 and 5) is reliably pressed against the arm 2. Preferably, six wavelengths are provided.

The body fat emitter 64 can contain any reasonable number of wavelengths. In the preferred embodiment, it is found that six wavelengths are sufficient for accurate body fat measurement. In a further embodiment body water is also measured at the same time. The same six different wavelengths are also preferred for measurement of body water.

Further chemical measurements are also made. Wavelengths associated with each further chemistry test are incorporated in the light wand 62. Specific additional analytes include hemoglobin and glucose.

Figure 8:
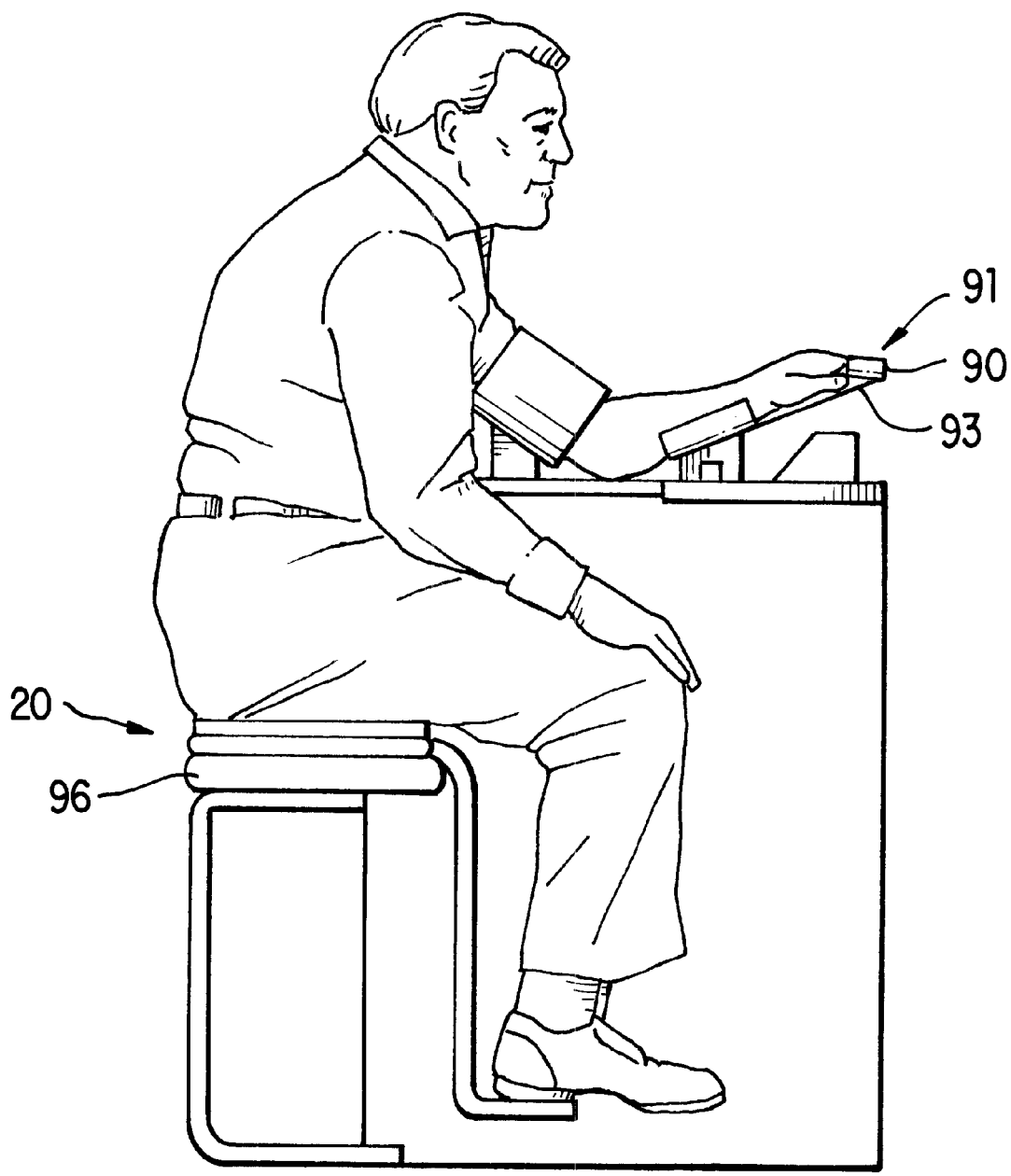
FIG. 8 is a further embodiment of the present invention in an apparatus measuring additional health parameters.

The embodiment of FIG. 8 is illustrated in the context of the system of FIG. 1. In the embodiment of FIG. 8, the apparatus 10 further comprises a finger measurement apparatus 90 comprising a tube 91 in which a finger may be inserted. The apparatus 90 includes analyte measurement means appeared such means are well-known in the art for performance of blood glucose measurement. Further analytes may also be measured. The finger measurement unit 90 is mounted to support means 93 on the arm support counter 28. The apparatus stand further includes a scale 96 mounted to the seat 20. For weight measurement, the user 1 lifts feet so as to support the user's weight on the scale 96.

30 Summarizing, present invention provides for reliable measurement of body fat in a self-service apparatus by an untrained user. Further, this measurement may be coordinated with the performance of measurement of other health parameters, particularly blood pressure heart rate and body weight. The measurements may further be coordinated with additional health parameter measurements in order to provide for simplified reliable and as comprehensive as permitted by the current state of diagnostic measurement. The foregoing specification has been written with a view toward enabling those skilled in the art to provide further embodiments in addition to those specifically illustrated above within the scope of the present invention.

What is claimed is:

1. A self-service body fat measurement apparatus comprising:
   a support means for receiving a user's arm, said support means including means for positioning an elbow of the arm at a spatial reference point;
   an arm tube for receiving an upper arm of the user;
   infrared body fat measurement means for measuring body fat of said user using infrared radiation; and
   means for maintaining said infrared body fat measurement means a substantially fixed distance from said spatial reference point and means for operating said infrared measurement means when said user's elbow is detected at said spatial reference.

2. Apparatus according to claim 1 where said means for maintaining said infrared measurement means the substantially fixed distance from said spatial reference point comprises an inflatable cuff mounted to said tube.

3. Apparatus according to claim 2 comprising means for inflating said cuff for providing a preselected pressure of said infrared measurement means against the arm.

4. Apparatus according to claim 3 wherein said cuff comprises a sphygmomanometer cuff and means for receiving said infrared measuring means.

5. Apparatus according to claim 4 further comprising means for inflating said sphygmomanometer cuff to a preselected maximum pressure, for allowing air to bleed from said sphygmomanometer cuff after said preselected pressure is reached and means for enabling said measurement after the pressure has decreased to a preselected level.

6. Apparatus according to claim 5 further comprising means for performing a blood pressure test on the user in conjunction with inflating and deflating said sphygmomanometer cuff.

7. Apparatus according to claim 6 further comprising a forearm rest angled for directing the person's elbow to said spatial reference point.

8. Apparatus according to claim 6 further comprising a memory sheet affixed to an outer surface of said sphygmomanometer cuff, said memory sheet having an outer surface facing an inner circumference of the tube, and means for closing said cuff around an arm of the person.

9. Apparatus according to claim 8 wherein said means for closing said cuff comprises a pulley selectively rotatable in either of a clockwise or counter clockwise direction;

a cable attachment point on an outer surface of the memory sheet; and first and second cables each extending from said cable attachment point to said pulley, one cable for being wound on said pulley when said pulley rotates in the clockwise direction, and the other cable for being wound on the pulley when said pulley rotates in the counterclockwise direction.

10. Apparatus according to claim 9 further comprising control means for stopping rotation of said pulley when a preselected tightness is measured around the person's upper arm.

11. Apparatus according to claim 2 further comprising means for measuring additional health parameters.

12. Apparatus according to claim 11 further comprising a seat on which said user sits when using said apparatus, and a scale in said seat for measuring the weight of said user and displaying said weight on a display.

13. Apparatus according to claim 12 further comprising finger measurement means for performing a finger diagnostic test.

14. Apparatus according to claim 2 further comprising finger measurement means for performing a finger diagnostic test.

15. A method for measuring body fat by an untrained user comprising the steps of selecting a spatial reference point in relation to an elbow of the user;

placing said elbow at said selected spatial reference point;

placing infrared test means adjacent an upper arm of the user on triceps at a fixed distance from said spatial reference point;

and performing said measurement.

16. A method according to claim 15 wherein the step of placing said measuring means against the forearm of the user comprises placing the forearm within a inflatable cuff and inflating said cuff to provide a predetermined pressure of the infrared means against the forearm.

17. A method according to claim 16 further comprising the step of inflating the cuff to a preselected maximum pressure, allowing air to bleed from the cuff and taking said measurement when the pressure decreases to a second preselected level.

18. A method according to claim 17 further comprising the step of performing blood pressure measurement in conjunction with inflation and deflation of the cuff.

* * * * *